(12) United States Patent
Gainer et al.

(10) Patent No.: US 9,180,131 B2
(45) Date of Patent: Nov. 10, 2015

(54) METHOD FOR CONTRACEPTION

(75) Inventors: Erin Gainer, Paris (FR); André Ulmann, Paris (FR); Luc Massart, Paris (FR); Héléne Guillard, Paris (FR)

(73) Assignee: LABORATOIRE HRA PHARMA, Paris (FR)

( * ) Notice: Subject to any disclaimer, the term of this patent is extended or adjusted under 35 U.S.C. 154(b) by 253 days.

(21) Appl. No.: 13/139,097

(22) PCT Filed: Dec. 11, 2009

(86) PCT No.: PCT/EP2009/066941
§ 371 (c)(1),
(2), (4) Date: Jun. 10, 2011

(87) PCT Pub. No.: WO2010/066883
PCT Pub. Date: Jun. 17, 2010

(65) Prior Publication Data
US 2011/0245211 A1    Oct. 6, 2011

Related U.S. Application Data

(60) Provisional application No. 61/121,963, filed on Dec. 12, 2008.

(51) Int. Cl.
*A61K 31/56* (2006.01)
*A61K 31/57* (2006.01)

(52) U.S. Cl.
CPC .................. *A61K 31/57* (2013.01); *A61K 31/56* (2013.01)

(58) Field of Classification Search
USPC .................................................. 514/170, 182
See application file for complete search history.

(56) References Cited

FOREIGN PATENT DOCUMENTS

WO    WO00/09136    2/2000
WO    WO03/045397    6/2003

OTHER PUBLICATIONS

Allen and Goldberg, Clinical Obstetrics and Gynecology, 2007;50(4):927-936.*
Creinin et al., Obstet Gynecol, 2006;108:1089-1097.*
Conard et al., Adolescent Medicine Clinics, 2005; 16: 585-562.*
Blithe et al., Sterpids, 2003;68(10-13): 1013-1017.*
Conard et al., Adolescent Medicine Clinics, 2005;16:585-562.*
International Search Report and Written Opinion dated Apr. 7, 2010 corresponding to International Patent Application No. PCT/EP09/66941.
Wellberry C., "Emergency Contraception," Archives of Family Medicine, American Med. Assoc., Chicago, IL., vol. 9, No. 7, Jul. 2000, pp. 642-646, XP002515431.
Orihuela Pedro A., "Drug Evaluation: Ulipristal, a progesterone receptor antagonist as a contraceptive and for the treatment of uterine fibroids," Current Opinion in Investigational Drugs, Pharmapress, US, vol. 8, No. 10, Oct. 2007, pp. 859-866, XP009115744.

* cited by examiner

*Primary Examiner* — San-Ming Hui
(74) *Attorney, Agent, or Firm* — Ascenda Law Group PC

(57) ABSTRACT

The invention relates to a method of contraception, which method comprises administering to a woman in need thereof an emergency contraception during one or two days, followed by a prolonged low dosage contraceptive treatment until next menstrual period.

4 Claims, No Drawings

METHOD FOR CONTRACEPTION

CROSS-REFERENCE TO A RELATED APPLICATION

The present application is a national stage application claiming priority based on PCT/EP2009/066941, filed Dec. 11, 2009, which claims priority based on U.S. Provisional Patent Application No. 61/121,963, filed Dec. 12, 2008.

FIELD OF THE INVENTION

The present invention relates to a new method for contraception. The invention also relates to a kit suitable for implementing said method. The invention is particularly adapted to emergency situations.

BACKGROUND OF THE INVENTION

Emergency contraception (EC) refers to back-up methods for contraceptive emergencies which women can use within the first few days after unprotected intercourse to prevent an unwanted pregnancy. The WHO-recommended regimen for emergency contraception is 1.5 mg levonorgestrel as a single dose. According to WHO, emergency contraceptives are usually not suitable for regular use (WHO. Medical eligibility criteria for contraceptive use. Third edition. Geneva, 2004; WHO. Selected practice recommendations for contraceptive use. Second edition. Geneva, 2005).

Conventional oral contraceptive (OC) starting instructions require waiting until menses to begin the OC. When a woman requires birth control at an office visit occurring between menses, many physicians delay starting hormonal contraceptives. However delaying contraception may place women at risk of unintended pregnancy until following menses. For this reason, it was proposed taking hormonal birth control products immediately after an office visit, at any point in the menstrual cycle, according to a "Quick Start" method (Lesnewski and Prine, Am Fam Physician, 2006, 74:105-12; Westhoff et al, Contraception, 2002, 66(3):141-5).

One important role emergency contraception pills could play is to serve as a gateway to longer-term method use (Don Downing presentation on behalf of the SC Emergency Contraception initiative, Mar. 12-16, 2007). In an over-the counter (OTC) environment e.g. where EC pills are accessed at pharmacies or drugstores and not family planning clinics, this may be more difficult to implement since there is no required visit to a clinician. Programs have then been developed in order to propose regular contraception to women using EC (ECAfrique bulletin, January 2008 vol 5/1).

SUMMARY OF THE INVENTION

The inventors now propose a "bridge" between an emergency contraception and a regular contraception, by initiating regular contraception immediately after an emergency contraception.

More specifically, the invention provides a method of contraception, which method comprises administering to a woman in need thereof an emergency contraception treatment during one or two days, followed by a prolonged low dosage contraceptive treatment until next menstrual period.

The contraceptive treatment preferably comprises the administration of one or several contraceptive agents selected from progestogen agents and progesterone receptor modulators.

In a preferred embodiment, the emergency contraception and the prolonged contraceptive treatments use a progestogen agent, which may be the same or different, more preferably an oral progestogen agent.

In this regard, a particular object of the present invention resides in a method of contraception, which method comprises administering to a woman in need of an emergency contraception a dosage of a progestogen agent of between 0.5 to 2 mg daily, during one or two days, followed by a dosage of a progestogen agent below 150 µg daily, until next menstrual period.

According to another embodiment, the emergency contraception and the prolonged contraceptive treatments use a progesterone receptor modulator, which may be the same or different, more preferably an oral progesterone receptor modulator.

The invention further provides a kit for implementing said method.

The invention further provides an emergency contraception agent or treatment for use in a woman during one or two days, followed by prolonged low dosage contraceptive treatment until next menstrual period.

The invention further provides the use of a progestogen agent or of a progesterone receptor modulator for the manufacture of a pharmaceutical composition intended for providing emergency contraception during one day or two days, followed by prolonged low dosage contraception until at least next menstrual period.

DETAILED DESCRIPTION OF THE INVENTION

As mentioned above, the invention resides in a method of contraception which comprises administering to a woman in need thereof an emergency contraception treatment during one or two days, followed by a prolonged low dosage contraceptive treatment until next menstrual period.

The Subject

The subject may be any woman in need of an emergency contraception.

Any woman of reproductive age may need emergency contraception at some point to avoid an unintended pregnancy. It is meant to be used in situations of unprotected intercourse, such as:
when no contraceptive has been used;
when there is a contraceptive failure or incorrect use, including:
  condom breakage, slippage, or incorrect use;
  non-compliance with dosage regimen for combined oral contraceptive pills;
  non-compliance with dosage regimen for progestogen-only pill (minipill);
  more than two weeks late for a progestogen-only contraceptive injection (depot-medroxyprogesterone acetate or norethisterone enanthate);
  more than seven days late for a combined estrogen-plus-progestogen monthly injection;
  dislodgment, delay in placing, or early removal of a contraceptive hormonal skin patch or ring;
  dislodgment, breakage, tearing, or early removal of a diaphragm or cervical cap;
  failed coitus interruptus (e.g., ejaculation in vagina or on external genitalia);
  failure of a spermicide tablet or film to melt before intercourse;
  miscalculation of the periodic abstinence method or failure to abstain on fertile day of cycle;

IUD expulsion; or in cases of sexual assault when the woman was not protected by an effective contraceptive method.

The Regimen

The contraceptive treatment according to the present invention comprises two phases: an emergency treatment, using high dosage of a contraceptive agent during a short period of time (1 or 2 days) followed by a prolonged contraceptive treatment, using a low dosage of a contraceptive agent until next menstrual period. As will be discussed, the contraceptive agent(s) used may be of various classes, and identical or different during each phase of the treatment. Furthermore, the contraceptive agent may be administered according to different routes.

More particularly, the emergency treatment phase is preferably a high dosage treatment, designed to administer within 1 or 2 days, an effective amount of a contraceptive agent to prevent ovulation.

In the case of a progestogen agent, the emergency treatment phase is designed to administer 0.5 to 2 mg daily of the progestogen agent, during one or two days, preferably a single dose of 1.5 mg, for one day, or a dose of 0.75 mg daily, during two consecutive days. Such a treatment is particularly adapted to an oral dosage of progestogen agent. As will be discussed below, a preferred progestogen agent is levonorgestrel. In this regard, in a preferred embodiment, the emergency treatment phase consists in an oral dosage of levonorgestrel of between 0.5 to 2 mg daily, during one or two days, preferably a single dose of 1.5 mg, or a dose of 0.75 mg daily, during two consecutive days.

In the case of a progesterone receptor modulator, the emergency treatment phase is designed to administer between 10 and 150 mg daily of the contraceptive agent, during one or two days. Such a treatment is particularly adapted to an oral dosage of progesterone receptor modulator.

The high dosage contraceptive treatment phase should be started as shortly as possible after unprotected intercourse, preferably within 5 days or less, more preferably within 3 days, even more preferably within 2 days or 24 hours or less after unprotected intercourse.

The high dosage treatment regimen is directly followed by a prolonged low dosage treatment regimen. Within the context of the present invention, "followed by" means the low dosage is started the day after the last high dose of contraceptive agent is taken. The low dosage regimen should be maintained until the next menstrual period.

Where the contraceptive agent is a progestogen agent, the low dosage generally consists in a dosage of said progestogen agent of below 150 μg daily, until next menstrual period.

Where the agent is a progesterone receptor modulator, the low dosage generally consists in a dosage of said agent of below 10 mg daily, until next menstrual period.

As indicated before, the contraceptive agent used for each phase of the treatment may be identical or not. Furthermore, as will be discussed below, the agent may be administered by various routes, e.g., orally, by injection, transdermally or vaginally.

In a particular embodiment, a progesterone receptor modulator is used for the emergency contraception phase, and a progestogen agent is used during the low dosage contraceptive treatment phase.

In a variant, a progestogen agent is used for the emergency contraception phase, and a progesterone receptor modulator is used during the low dosage contraceptive treatment phase.

In a particular embodiment of the invention, the woman is administered with an oral dosage of a progestogen agent of between 0.5 to 2 mg daily, during one or two days, followed by an oral dosage of a progestogen agent below 150 μg daily, until next menstrual period. In a preferred embodiment, the progestogen agent used is the same throughout the entire treatment. In a most preferred embodiment, the agent is levonorgestrel.

In another particular embodiment, the woman is administered with a single dose of 1.5 mg of levonorgestrel, followed by a daily dosage of 30 μg of levonorgestrel until next menstrual period.

In another particular embodiment, the woman is administered with a daily dose of 0.75 mg of levonorgestrel during two consecutive days, followed by a dosage of 30 μg of levonorgestrel until next menstrual period.

Depending on the starting period of the treatment, the low dosage phase may last several days and up to e.g., 28 days or more. Once the next menstrual period has started, the treatment can be stopped. At the end of the treatment, regular contraception may be resumed or started, with the same or a different regiment.

The Contraceptive Agent

The contraceptive treatment according to the present invention comprises two phases: an emergency treatment, using high dosage of a contraceptive agent during a short period of time (1 or 2 days), and a prolonged contraceptive treatment, using a low dosage of a contraceptive agent until next menstrual period. The contraceptive agents used may be of various classes, and identical or different during each phase of the treatment.

More particularly, the contraceptive agent(s) may be selected from progestogen agents or from progesterone receptor modulators. It should be understood that the contraceptive treatment of this invention is, most preferably, a non-estrogenic treatment (i.e., it is not used in combination with estrogens).

Progestogen Agents:

The progestogen agents, also designated progestins, may be any progestationally active compound.

The progestogen agents may be selected from progesterone and its derivatives such as, for example, 17-hydroxy progesterone esters, 19-nor-17-hydroxy progesterone esters, 17.alpha.-ethinyltestosterone and derivatives thereof, 17.alpha.-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, DL-norgestrel, D-17.alpha.-acetoxy-13.beta.-ethyl-17.alpha.-ethinyl-gon-4-en-3-one oxime, gestodene, desogestrel, norgestimate, nestorone and drospirenone.

In a preferred embodiment, the progestogen agent used in the first phase (e.g., at a dosage of 0.5 to 2 mg daily), is the same as the one used in the second phase of the treatment (e.g., at a dosage below 150 μg daily).

The preferred progestogen agent is levonorgestrel. In a particular embodiment of the invention, the levonorgestrel is used both for the high dosage treatment phase (at a dosage of 0.5 to 2 mg daily) and for the prolonged contraception treatment phase (at a dosage below 150 μg daily).

In a preferred embodiment, it is to be understood that the progestogen agent is not combined with any other hormonal contraceptive agent, such as an estrogen. In that case, the contraceptive is often referred to as a "progestin-only" contraceptive.

Progesterone Receptor Modulators

Progesterone receptor modulators for use in the present invention may be selected from e.g., ulipristal acetate, mifepristone or CDB-4124 or active metabolites thereof.

The preferred progesterone receptor modulator is ulipristal acetate.

Ulipristal acetate, formerly known as CDB-2914, designates within the context of this application 17α-acetoxy-11β-[4-N,N-dimethylamino-phenyl]-19-norpregna-4,9-diene-3,20-dione, represented by formula I:

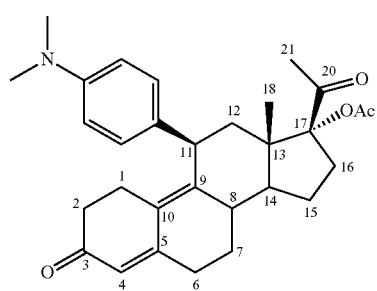

Ulipristal acetate, and methods for its preparation, are described e.g., in U.S. Pat. Nos. 4,954,490; 5,073,548; and 5,929,262, as well as in international patent applications WO2004/065405 and WO2004/078709.

In a particular embodiment of the invention, ulipristal acetate is used both for the high dosage treatment phase (at a dosage of 10 to 100 mg daily) and for the prolonged contraception treatment phase (at a dosage below 10 mg daily), or it is used for the high dosage treatment phase while a progestogen agent is used for the prolonged contraception treatment phase.

Administration Routes and Formulation

The contraceptive agents may be administered by various routes, e.g., orally, by injection, transdermally or vaginally. A preferred administration route is the oral route. However, the agent may also be administered by injection, or with a patch, in a gel, or a vaginal ring, for instance.

Oral solid dosage forms are preferentially compressed tablets or capsules. Compressed tablets may contain any excipients which are diluents to increase the bulk of the active ingredient so that production of a compressed tablet of practical size is possible. Binders, which are agents which impart cohesive qualities to powdered materials are also necessary. Starch, gelatine, sugars such as lactose or dextrose, and natural and synthetic gums are used. Disintegrants are necessary in the tablets to facilitate break-up of the tablet. Disintegrants include starches, clays, celluloses, algins, gums and crosslinked polymers. Lastly small amounts of materials known as lubricants and glidants are included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants. Procedures for the production and manufacture of compressed tablets are well known by those skilled in the art.

Capsules are solid dosage forms using preferentially either a hard or soft gelatine shell as a container for the mixture of the active ingredient and inert ingredients. Procedures for production and manufacture of hard gelatin and soft elastic capsules are well known in the art.

As far as the phase of low dosage contraception is concerned, buccal forms or devices are also useful, such as those described in U.S. patent application 20050208129, herein incorporated by reference. U.S. patent application 20050208129 describes a prolonged release bioadhesive mucosal therapeutic system containing at least one active principle, with an active principle dissolution test of more than 70% over 8 hours and to a method for its preparation. Said bioadhesive therapeutic system comprises quantities of natural proteins representing at least 50% by weight of active principle and at least 20% by weight of said tablet, between 10% and 20% of an hydrophilic polymer, and compression excipients, and comprising between 4% and 10% of an alkali metal alkylsulphate to reinforce the local availability of active principle and between 0.1% and 1% of a monohydrate sugar.

The Kit:

In accordance with the present invention is provided a contraceptive kit comprising
- one or more unit doses of contraceptive agent for emergency contraception, preferably in oral form intended for administration during one or two days;
- one or more cycle packs of contraceptive agent for prolonged low dosage contraception, intended for administration of less than 150 μg daily.

In a preferred embodiment, the kit comprises
- one or more unit doses of oral progestogen agent intended for administration of 0.5 to 2 mg daily, during one or two days;
- one or more cycle packs of oral progestogen agent for prolonged low dosage contraception, intended for administration of less than 150 μg daily.

Cycle pack, as used herein, refers to an oral contraceptive pill pack generally containing from 21-28 consecutive days of active ingredient-containing dosage units and may also contain placebos for the remainder of the cycle (3 to 7 days), which are free of hormonal active ingredient. Dosage units in the form of tablets or capsules may also contain excipients such as binders, diluents, disintegrating agents and lubricating agents. Placebos of the cycle pack may contain non-hormonal active agents such as iron or folic acid.

In a preferred embodiment, it is provided a kit comprising
- a unit dose of 0.75 mg of oral progestogen agent, such as levonorgestrel;
- at least 14, preferably at least 21 to 28 unit doses of 30 μg of oral progestogen agent, such a levonorgestrel.

The invention claimed is:

1. A method of contraception, comprising the steps of:
   administering to a woman in need thereof ulipristal acetate as an emergency contraception treatment during one or two days at a daily dosage of 10 to 100 mg, wherein the administration of ulipristal acetate is oral and performed within about 5 days after unprotected intercourse, and
   providing the woman with low dosage contraception treatment until the woman's next menstrual period, by administering to the woman a contraceptive comprising a progesterone receptor modulator at a daily dosage of lower than 10 mg.

2. The method of claim 1, wherein the progesterone receptor modulator is ulipristal acetate.

3. The method of claim 1, wherein the contraceptive comprising a progesterone receptor modulator is administered by oral route.

4. A method of contraception, comprising:
   administering to a woman in need thereof ulipristal acetate as an emergency contraception treatment during one or two days at a daily dosage of 10 to 100 mg, wherein the administration of ulipristal acetate is oral and performed within 5 days after unprotected intercourse, followed by administering to the woman ulipristal acetate at a daily oral dosage below 10 mg until the woman's next menstrual period.

* * * * *